(12) United States Patent
Sudo et al.

(10) Patent No.: US 7,221,388 B2
(45) Date of Patent: May 22, 2007

(54) ENDOSCOPE IMAGE SENSING METHOD AND APPARATUS

(75) Inventors: Masaru Sudo, Hachioji (JP); Kanichi Matsumoto, New York, NY (US)

(73) Assignee: Olympus Optical Co., Ltd., Tokyo (JP)

( * ) Notice: Subject to any disclaimer, the term of this patent is extended or adjusted under 35 U.S.C. 154(b) by 203 days.

(21) Appl. No.: 10/984,916

(22) Filed: Nov. 9, 2004

(65) Prior Publication Data

US 2005/0068427 A1  Mar. 31, 2005

Related U.S. Application Data

(62) Division of application No. 09/496,061, filed on Feb. 1, 2000.

(30) Foreign Application Priority Data

Feb. 4, 1999  (JP) .................... 11-027354

(51) Int. Cl.
   *H04N 7/18*  (2006.01)
(52) U.S. Cl. .................. 348/71; 348/68; 348/69; 348/65; 348/77; 348/302; 348/70; 348/76; 600/101; 600/109; 600/160; 600/178
(58) Field of Classification Search .............. 348/71, 348/68, 65, 69, 70, 77, 302, 76; 600/101, 600/109, 160, 178
See application file for complete search history.

(56) References Cited

U.S. PATENT DOCUMENTS

| | | | | |
|---|---|---|---|---|
| 4,805,016 A | | 2/1989 | Kato | |
| 4,875,091 A | * | 10/1989 | Yamada et al. | 348/269 |
| 4,924,856 A | * | 5/1990 | Noguchi | 348/70 |
| 5,032,913 A | | 7/1991 | Hattori et al. | |
| 5,181,100 A | * | 1/1993 | Hodgson | 348/594 |
| 5,339,159 A | | 8/1994 | Nakamura et al. | |
| 5,408,263 A | | 4/1995 | Kikuchi et al. | |
| 5,833,617 A | * | 11/1998 | Hayashi | 600/476 |
| 6,080,104 A | | 6/2000 | Ozawa et al. | |

FOREIGN PATENT DOCUMENTS

| | | |
|---|---|---|
| JP | 6-125871 A | 5/1994 |
| JP | 06-315463 A | 11/1994 |
| JP | 07-298293 A | 11/1995 |
| JP | 08-46980 A | 2/1996 |
| JP | 10-211166 A | 8/1998 |
| JP | 10-290469 A | 10/1998 |

* cited by examiner

*Primary Examiner*—Shawn S. An
(74) *Attorney, Agent, or Firm*—Frishauf, Holtz, Goodman & Chick, P.C.

(57) ABSTRACT

This invention relates to an endoscope image sensing apparatus which can switch suitable color matrixes in accordance with the type of observation region, the type of light source used, or the like, and obtain good color reproduction corresponding to the type of observation region or the type of light source used. This apparatus uses a one-chip color CCD as an image sensing means. A CPU reads out corresponding color matrix coefficients from a ROM, and outputs the coefficients to a color separation circuit. The color separation circuit executes a matrix computation based on the color matrix to convert luminance and color difference signals into primary color signals.

9 Claims, 9 Drawing Sheets

ENDOSCOPE IMAGE SENSING METHOD AND APPARATUS

CROSS-REFERENCE TO RELATED APPLICATIONS

The present application is a divisional application of U.S. application Ser. No. 09/496,061, filed Feb. 1, 2000 now abandoned.

BACKGROUND OF THE INVENTION

The present invention relates to an endoscope image sensing method and apparatus which are suitable for every observation region and realize color reproduction independent of the type of light source.

In general, for endoscope image sensing apparatuses for sensing an object by using an image sensing device such as a CCD (Charge Coupled Device), and obtaining a video signal by photoelectrically converting the sensed image data, it is important to ensure good color reproduction by eliminating variations resulting from different types of light sources and the like. To realize such good color reproduction, various types of adjustments such as white balance adjustment and black balance adjustment are performed.

For example, Jpn. Pat. Appln. KOKAI Publication No. 10-211166 discloses a technique associated with an endoscope image sensing apparatus which realizes good color reproduction by performing white balance and black balance adjustments. This apparatus is further characterized by preventing erroneous use of the white balance and black balance adjustments.

In an endoscope image sensing apparatus using an image sensing device such as a CCD as described above, the luminance and color difference signals obtained by the image sensing device are arithmetically processed by using a uniquely defined matrix (to be referred to as a color matrix hereinafter) consisting of predetermined coefficients, thereby converting the signals into R, G, and B digital signals. The image represented by the signals is then displayed on the screen of a monitor or the like.

Figure 8:
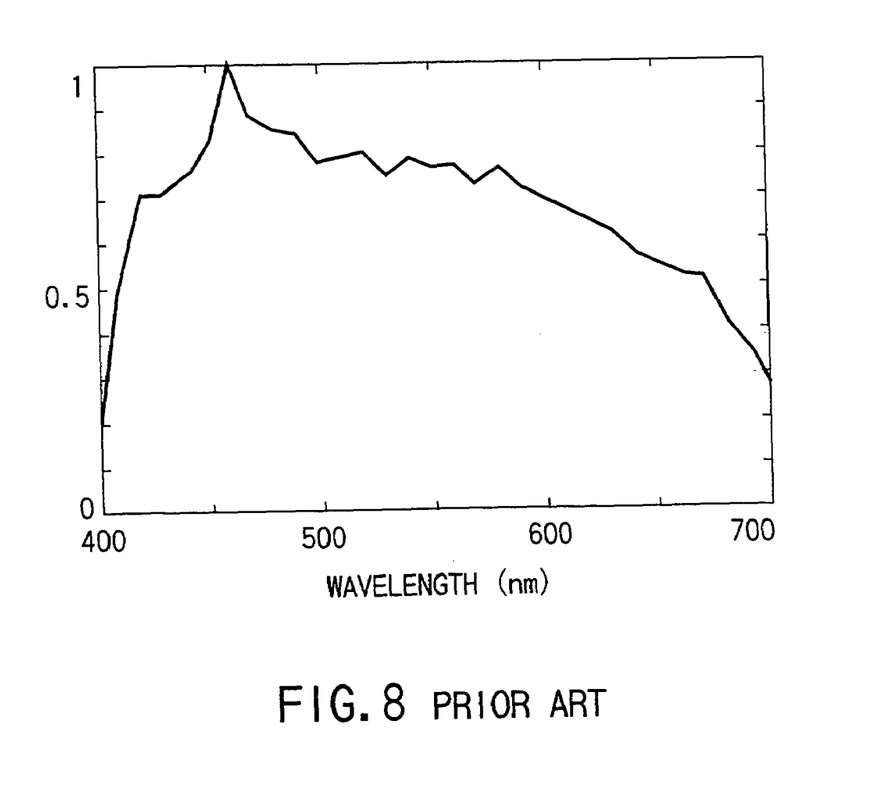
FIG. 8 is a graph showing the spectral characteristics of a xenon lamp.
Figure 9:
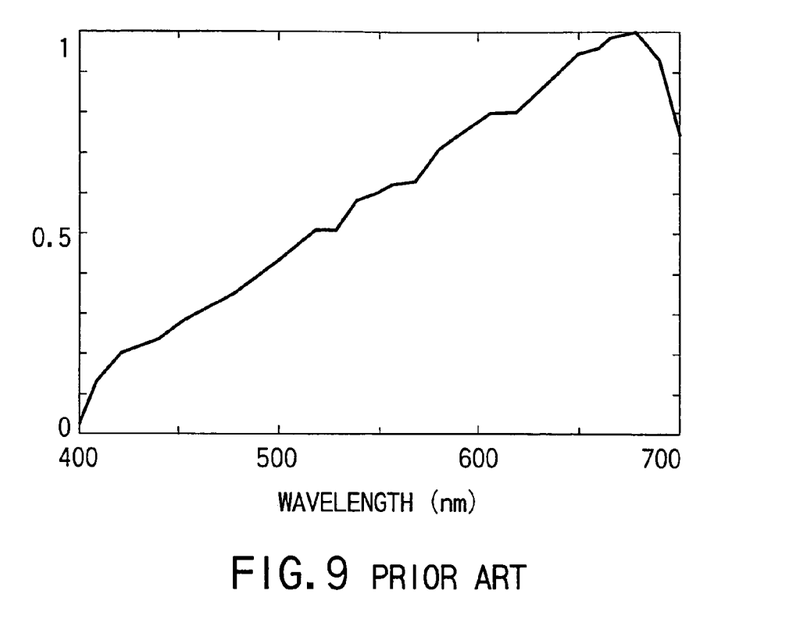
FIG. 9 is a graph showing the spectral characteristics of a halogen lamp.
Figure 10:
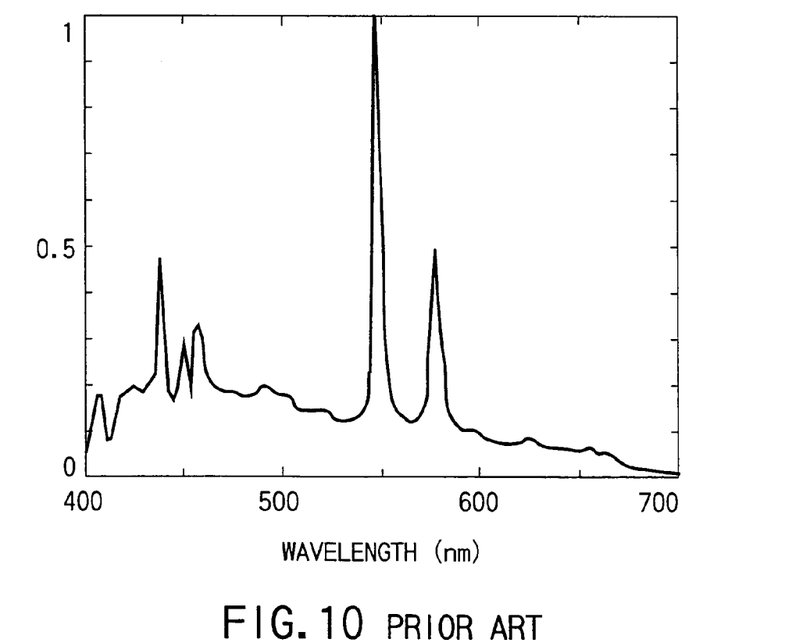
FIG. 10 is a graph showing the spectral characteristics of a metal halide lamp.

Endoscope image sensing apparatuses generally use various types of light sources. For example, FIGS. 8 to 10 respectively show the spectral characteristics of a xenon lamp, halogen lamp, and metal halide lamp. More specifically, FIG. 8 shows the spectral characteristics of a xenon lamp, which are similar to those of natural light and substantially uniform throughout the ultraviolet, visible, and infrared regions. FIG. 9 shows the spectral characteristics of a halogen lamp, which exhibit high output levels across the visible and infrared regions. FIG. 10 shows the spectral characteristics of a metal halide lamp, which exhibit high output levels in the visible region.

In endoscopic diagnoses, different color reproduction are desired depending on the observation regions. For this reason, as in the prior art, it is difficult to realize desired color reproduction by using only a uniquely defined color matrix regardless of the observation region or light source to be used.

Figure 11:
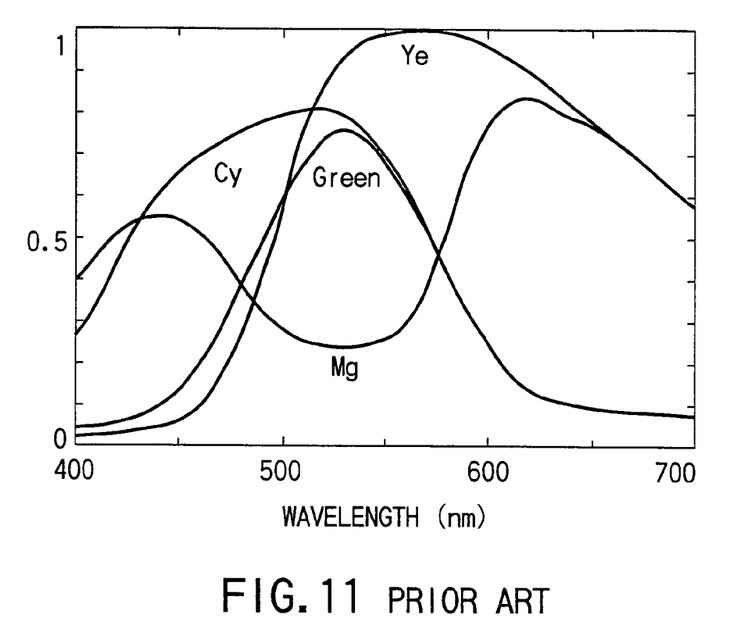
FIG. 11 is a graph showing the spectral sensibility characteristics of a CCD output.
Figure 12:
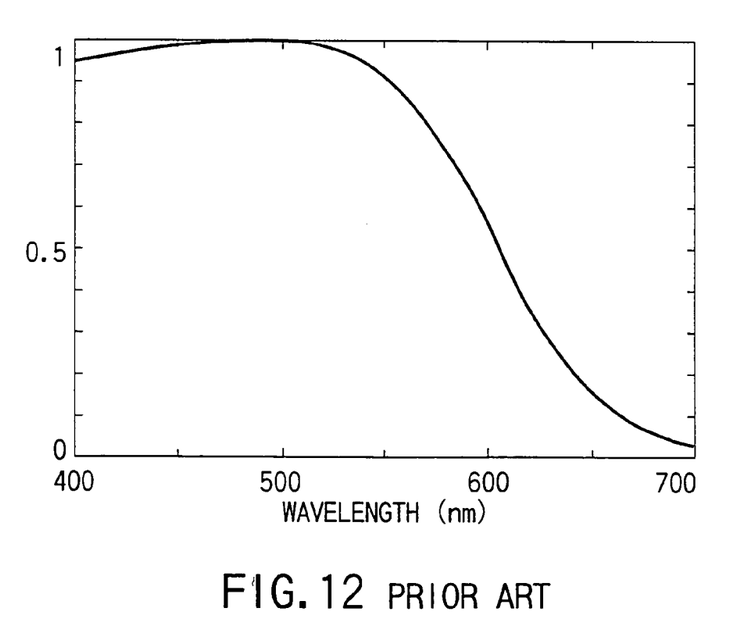
FIG. 12 is a graph showing the spectral characteristics of an infrared cut filter.

If, for example, a one-chip CCD is used, a signal obtained by combining an output from the CCD having spectral sensitivity characteristics like those shown in FIG. 11, an output from an infrared cut filter having spectral characteristics like those shown in FIG. 12, and an output form a light source having spectral characteristics like those shown in one of FIGS. 8 to 10 is input to an Y/C separation circuit. If arithmetic operation is performed by using the uniquely defined color matrix described above after the signal is subjected to Y/C separation processing, the operation result varies depending on the light source used. As a consequence, the color reproduction yields different results.

Figure 13:
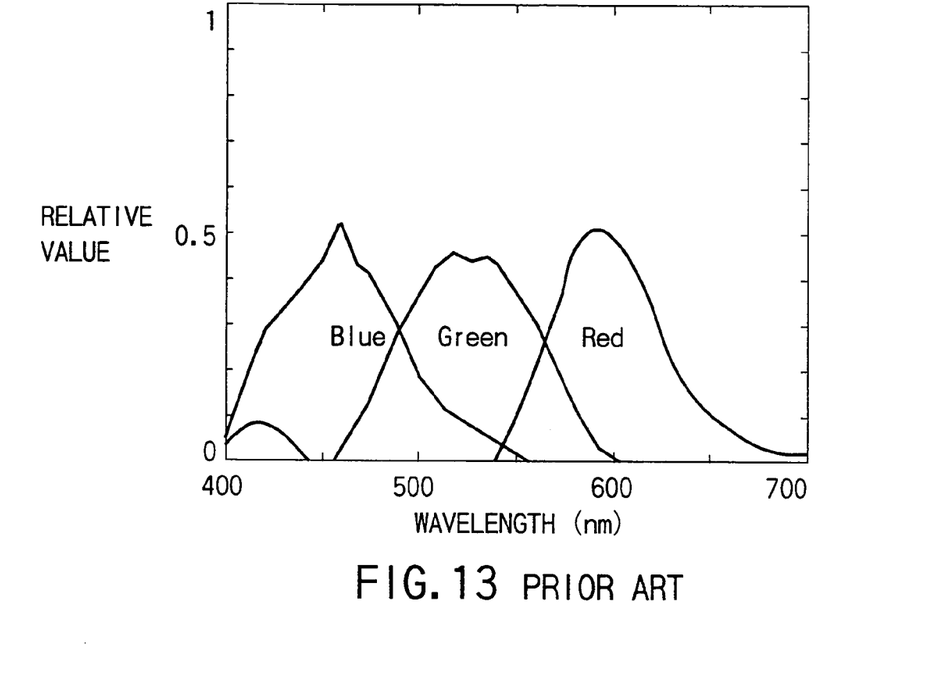
FIG. 13 is a graph showing the spectral characteristics (with a xenon lamp ON) after matrix arithmetic processing.
Figure 14:
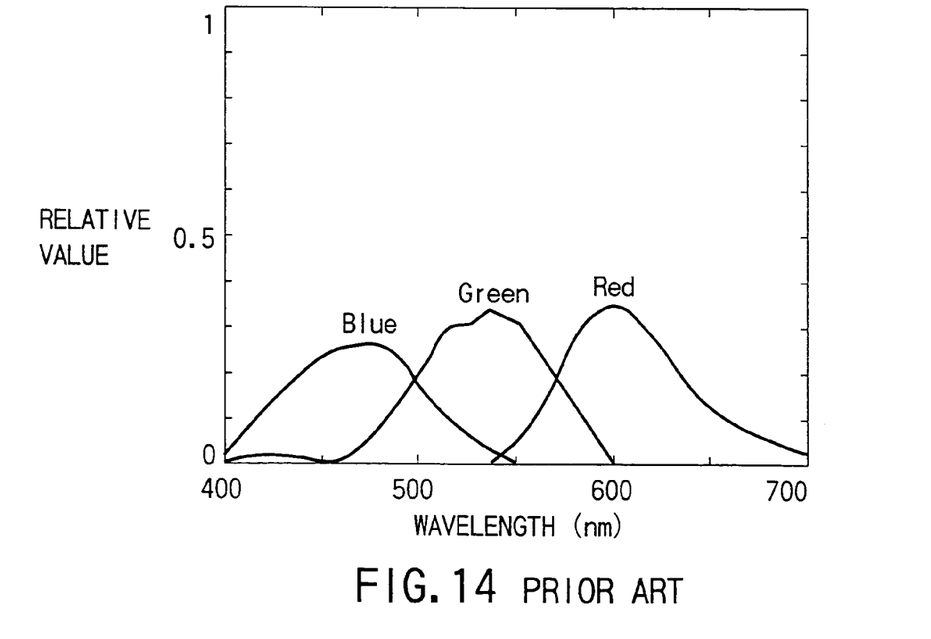
FIG. 14 is a graph showing the spectral characteristics (with a halogen lamp ON) after matrix arithmetic processing.

For example, FIG. 13 shows the characteristics obtained by matrix operation using a xenon lamp as a light source. FIG. 14 shows the characteristics obtained by matrix operation using a halogen lamp as a light source. Obviously from the two graphs, the color reproduction result in one operation differ from that in the other operation.

BRIEF SUMMARY OF THE INVENTION

The present invention has been made in consideration of the above problems, and has as its object to provide an endoscope image sensing apparatus which can switch to a suitable color matrix in accordance with the type of observation region, the type of light source used, or the like, and obtain good color reproduction corresponding to the type of observation region or the type of light source used.

In order to achieve the above object, according to the first aspect of the present invention, there is provided an endoscope image sensing apparatus comprising an image sensing section for obtaining an image signal by photoelectrically converting an object image, a conversion matrix section capable of changing a setting associated with a conversion matrix to a desired setting, the conversion matrix being used to convert the image signal, obtained by the image sensing section, into a video signal, by a predetermined matrix computation, and an input section for inputting information about a change in the setting associated with the conversion matrix.

According to the second aspect, there is provided an endoscope image sensing apparatus comprising an image sensing section for obtaining a image signal by photoelectrically converting an object image, a conversion matrix section for converting the image signal obtained by the image sensing section into a video signal by a predetermined matrix computation, a designating section for designating a change of a setting associated with conversion performed by the conversion matrix section, and a control section for changing a setting associated with the conversion performed by the conversion matrix section on the basis of designation performed by the designating section.

According to the third aspect, there is provided an endoscope image sensing apparatus comprising a light source for irradiating an object with light, an image sensing section for obtaining a image signal by photoelectrically converting an object image, a conversion matrix section for converting the image signal obtained by the image sensing section into a video signal by a predetermined matrix computation, a communication section for performing serial communication with the light source, and a control section for performing serial communication with the light source through the communication section, receiving an identification signal associated with the light source, recognizing a type of light source, and changing a setting associated with conversion performed by the conversion matrix section on the basis of the type.

According to the fourth aspect, there is provided an endoscope image sensing apparatus comprising, a light source for irradiating an object with light, an image sensing section for obtaining an image signal by photoelectrically converting an object image, a conversion matrix section for converting the image signal obtained by the image sensing section into a video signal by a predetermined matrix computation, a white balance processing section for performing white balance processing, and a control section for recognizing a type of light source on the basis of a magnitude of a gain coefficient set when the white balance processing is performed, and changing the setting associated with the conversion matrix section on the basis of the type of light source.

According to the fifth aspect, there is provided an endoscope image sensing method comprising the steps of obtaining an image signal by photoelectrically converting an object image, changing a setting associated with a conversion matrix to a desired setting, the conversion matrix being used to convert the image signal, obtained in the step of performing image sensing, into a video signal, by a predetermined matrix computation, and inputting information about a change in the setting associated with the conversion matrix.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The embodiments of the present invention will be described below with reference to the views of the accompanying drawing.

Figure 1:
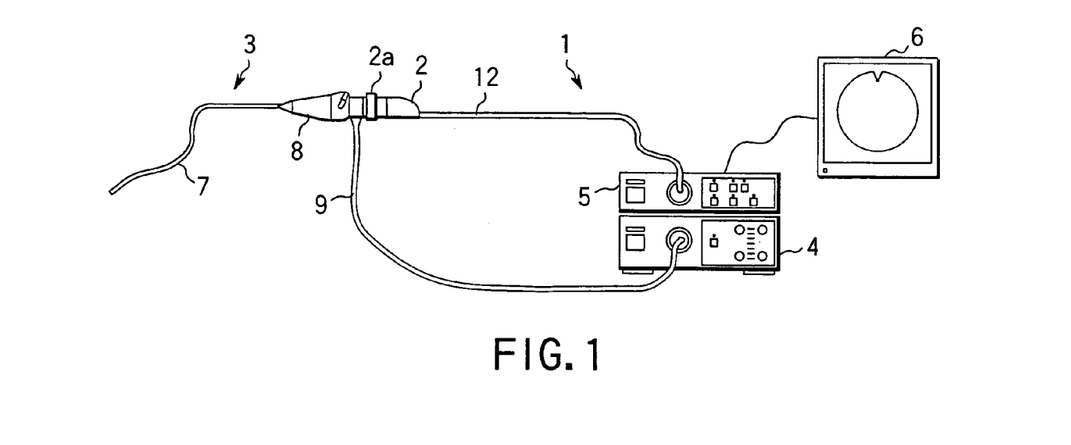
FIG. 1 is a schematic view showing the arrangement of an endoscope image sensing apparatus of the present invention.

FIG. 1 is a conceptual view of an endoscope image sensing apparatus of the present invention. An overview of this apparatus will be described below.

As shown in FIG. 1, an endoscope image sensing apparatus 1 of the present invention is comprised of a camera head 2 incorporating a CCD, a scope 3 to which the camera head 2 is detachably connected, a light source section 4 for supplying illumination light to the scope 3, a camera control unit (to be abbreviated to CCU hereinafter) 5 serving as a processor for performing signal processing for the CCD incorporated in the camera head 2, and a TV monitor 6 for displaying a standard video signal having undergone signal processing in the CCU 5.

The scope 3 is, for example, an optical endoscope having an insertion portion 7 in which an elongated, flexible image guide fiber (not shown) for transmitting an endoscopic image is inserted.

When the camera head 2 is detachably connected to the eyepiece of an operation portion 8 formed on the proximal end of the insertion portion 7 through an adaptor 2a, the endoscopic image sent to the eyepiece of the operation portion 8 through the image guide fiber (not shown) can be sensed by the camera head 2. A light guide cable 9 extends from the operation portion 8 of the scope 3. When the distal end of the light guide cable 9 is connected to the light source section 4, illumination light supplied from the light source section 4 is sent from the distal end of the scope 3 onto an object (not shown) through the light guide (not shown) inserted in the insertion portion 7.

When the endoscope image sensing apparatus 1 is used, the light guide cable 9 of the scope 3 is attached to the light source section 4. With this operation, although not shown, illumination light from the lamp of the light source section 4 passes through a stop, is focused by a lens, and strikes the opposing end face of the light guide. This illumination light is sent to the scope 3 through the light guide, passes through the scope 3, and exits forward from the distal end of the scope 3. An object such as a body cavity of a patient is then irradiated with the illumination light. The light reflected by the object irradiated with the illumination light is formed into an image by the scope 3, and the object is sensed by the CCD in the camera head 2 through the scope 3.

In the camera head 2, the CCD is positioned at the focal plane of the image sensing lens so that an object image is formed on the image sensing plane of the CCD to be photoelectrically converted. This CCD is connected to the CCU 5 through a camera cable 12 which extends from the camera head 2 and in which a CCD driving signal transmission line and CCD output signal transmission line are inserted. An output signal form the CCD is sent to the CCU 5 to be subjected to various signal processes. The video signal output from the CCU 5 is sent to the TV monitor 6 to display an observation image of the object on the TV monitor 6.

In the arrangement described above, at the time of observation, the insertion portion 7 of the scope 3 is inserted into a body cavity, illumination light is supplied from the light source section 4 to the scope 3, and the endoscopic image sent to the eyepiece is sensed by the CCD of the camera head 2. This image signal is subjected to predetermined signal processing in the CCU 5 first, and then output to the TV monitor 6, thereby displaying an observation image on the TV monitor 6.

It is assumed that a one-chip color CCD is used in the present invention. Therefore, the video signal obtained by the CCD is separated into a luminance signal Y and chrominance signal C after predetermined processing. These signals are further separated into the luminance signal Y and color difference signals R-Y (Cr) and B-Y (Cb). By multiplying these signals by color matrix coefficients, R, G, and B signals can be obtained.

The color reproduction result of an observation image is determined by the above color matrix coefficients. The present invention is characterized in that a plurality of color matrixes are prepared, and suitable one of the color matrixes can be selected by manual or automatic switching operation using a switching means (to be described in detail later).

For example, in the present invention, three types of lamps, namely a xenon lamp, halogen lamp, and metal halide lamp, are assumed as light source sections 4. The spectral characteristics of these lamps have already been shown in FIGS. 8 to 10. As described above, since the different light source sections 4 exhibit different characteristics, desired color reproduction may not be obtained by arithmetic processing which uses a single color matrix as in the prior art. In consideration of this problem, according to the present invention, a color matrix can be selected in accordance with the type of light source to realize color reproduction independent of the light source. This will be described in detail later in each embodiment.

Endoscope image sensing apparatuses according to the first to third embodiments using different methods of switching the above color matrix coefficients will be described in detail below.

The first embodiment of the present invention will be described first.

Figure 2:
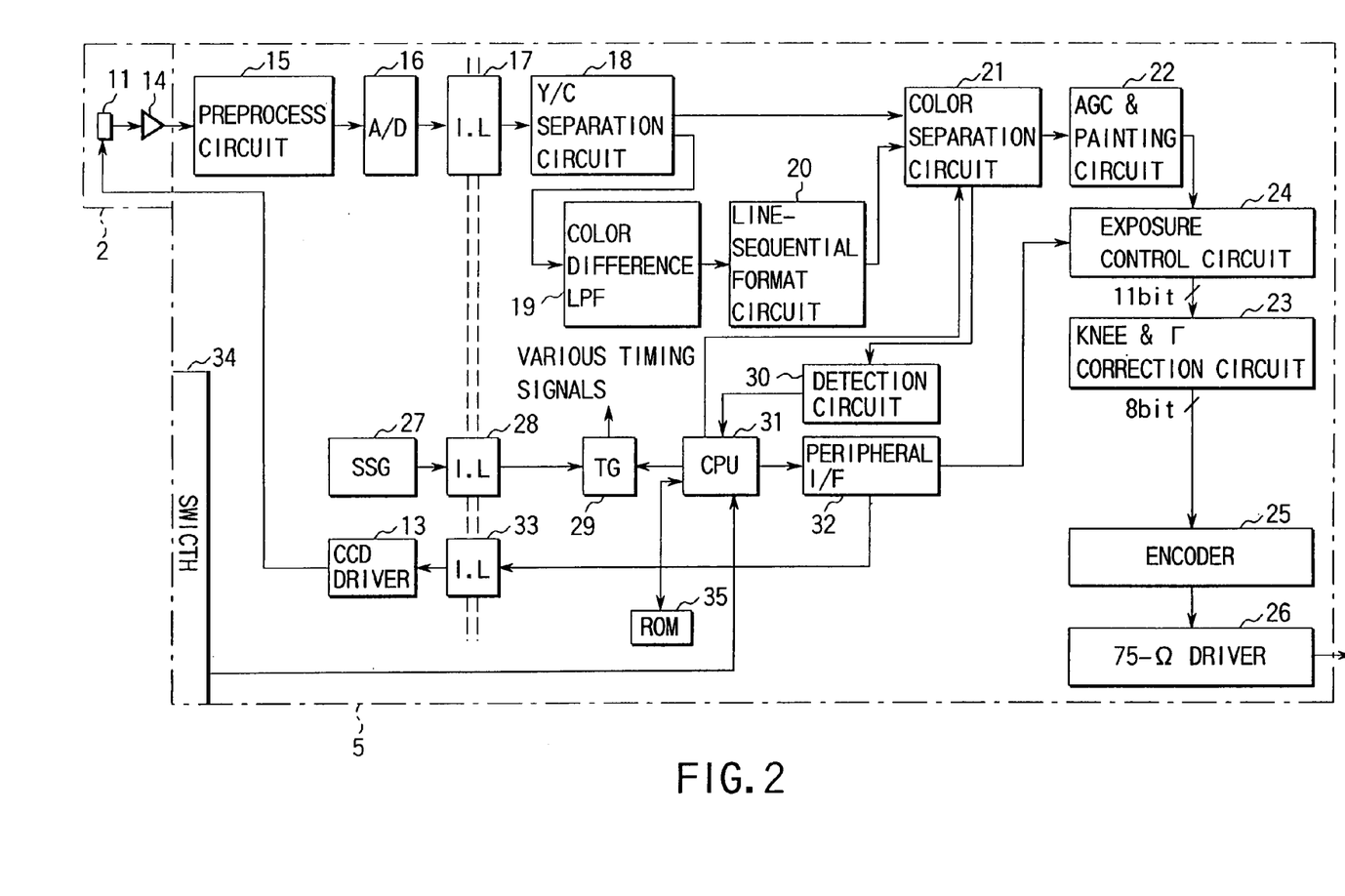
FIG. 2 is a block diagram showing the arrangement of an endoscope image sensing apparatus according to the first embodiment.

FIG. 2 is a block diagram showing the arrangement of the endoscope image sensing apparatus according to the first embodiment of the present invention. The first embodiment is characterized in that a CPU 31 reads out coefficients of a predetermined color matrix from a table of a ROM 35 on the basis of the operation of a switch 34 by the user, and perform predetermined image processing for color reproduction on the basis of the color matrix coefficients. This characteristic feature will be described in detail below.

As shown in FIG. 2, a CCU 5 incorporates a CCD driver 13 for driving/controlling a CCD 11. The CCD driver 13 supplies a CCD driving signal to the CCD 11 through a CCD driving signal transmission line in a camera cable 12. The signal charge stored in the CCD 11 is read out as a CCD output signal.

The CCD output signal read out from the CCD 11 is amplified by a preamplifier 14 and sent to the CCU 5 through a CCD output signal transmission line in the camera cable 12. This signal is input to a preprocess circuit 15 in the CCU 5.

An A/D conversion circuit 16, isolation circuit (to be abbreviated to I. L hereinafter) 17, and Y/C separation circuit 18 are connected to the output stage of the preprocess circuit 15. The CCD output signal input to the preprocess circuit 15 is subjected to preprocesses such as CDS (Correlation Double Sampling) and S/H (Sampling/Holding). The resultant signal is input to the A/D conversion circuit 16 to be converted into a digital signal. This digital signal is electrically isolated by the I. L 17 and input to the Y/C separation circuit 18.

A color difference LPF (Low-Pass Filter) 19, a line-sequential format circuit 20, and a color separation circuit 21 constituted by an RGB matrix are connected to the output stage of the Y/C separation circuit 18. The digital signal input to the Y/C separation circuit 18 is separated into the luminance signal Y and the chromatic signal C. Pseudo color components and the like are removed from the chromatic signal C by the color difference LPF 19 and the signal is converted into line-sequential signals by the line-sequential format circuit 20. As a consequence, three digital signals Y, Cr, and Cb are input to the color separation circuit 21. These signals are converted into R, G, and B digital signals by the color separation circuit 21.

When the above digital signals Y, Cr, and Cb of the three systems are to be converted into the R, G, and B signals, the CPU 31 reads out corresponding coefficients (color matrix) from the table held beforehand in the ROM 35 in accordance with an operation command from the switch 34 operated by the user, and performs a predetermined arithmetic operation for realizing desired color reproduction. This operation is a characteristic feature of the present invention and will be described in detail later.

An AGC & painting circuit 22, exposure control circuit 24, and knee & γ correction circuit 23 are connected to the output stage of the color separation circuit 21. The R, G, and B signals from the color separation circuit 21 are subjected to gain adjustment and painting processing in the AGC & painting circuit 22. The resultant signals undergo exposure control processing in the exposure control circuit 24. The knee & γ correction circuit 23 then performs knee processing and nonlinear γ correction processing to compress the information of the high-luminance portion of each signal.

For example, a digital signal (input) consisting of 11-bit data and input from the input stage is compressed into an 8-bit digital signal (output) by the knee processing and γ processing in the knee & γ correction circuit 23. An encoder 25 is connected to the output stage of the knee & γ correction circuit 23 to convert each signal into a standard TV signal, e.g., an NTSC signal. This signal is impedance-matched by a 75-Ω driver 26 and output to a TV monitor 6.

The CCU 5 has a reference signal generating circuit (to be abbreviated to SSG hereinafter) 27. A timing signal generating circuit (to be abbreviated to TG hereinafter) 29 generates various timing signals to the respective circuits described above on the basis of the reference clock signals generated by the SSG 27 and electrically isolated by an I. L 28.

The CCU 5 also includes a detection circuit 30 for detecting the brightness of an image based on the R, G, and B signals from the color separation circuit 21. The detection output from this detection circuit 30 is output to the CPU 31. The CPU 31 then checks whether the brightness of the image is equal to or higher than a predetermined level, and controls a peripheral interface (to be referred to as a peripheral I/F hereinafter) 32 on the basis of the brightness of the image. As a consequence, the peripheral I/F 32 outputs a setting signal and control signal to the exposure control circuit 24 and CCD driver 13.

The control signal from the peripheral I/F 32 to the CCD driver 13 is electrically isolated by an I. L 33. These I. LS 17, 28, and 33 are used to secure safety by electrically isolating the scope 3 side from the CCU 5 side because the endoscope image sensing apparatus 1 is a medical device.

The exposure control circuit 24 is comprised of first and second coefficient registers for receiving a field signal from the TG 29 and a setting signal from the peripheral I/F 32 controlled by the CPU 31, discriminating a 1-field period on the basis of an edge of the field signal, and outputting a coefficient signal corresponding to the setting signal from the peripheral I/F 32 in synchronism with each 1-field period, a first multiplier for multiplying each of 11-bit R, G, and B digital signals received through the AGC & painting circuit 22 by the coefficient signal from the first coefficient register, a delay circuit having a field memory for delaying each of the R, G, and B digital signals received through the AGC & painting circuit 22 by a 1-field period, and a second multiplier for multiplying each of the R, G, and B digital signals, delayed by the delay circuit by a 1-field period, by the coefficient signal from the second coefficient register. The exposure control circuit 24 is comprised of an adder for adding the outputs from the first and second multipliers, a delay circuit for delaying the output from the adder by a 1-field period, and an interpolation circuit for interpolating the output from the delay circuit.

The first embodiment having the above arrangement is characterized in that a color matrix to be used for conversion of the three digital signals Y, Cr, and Cb into the R, G, and B digital signals in the color separation circuit 21 can be selected on the basis of the operation of the switch 34 by the user.

More specifically, when the user operates the switch 34, the CPU 31 reads out the color matrix corresponding to the operation command by referring to the table held beforehand in the ROM 35, and outputs the color matrix to the color separation circuit 21, thereby performing predetermined arithmetic processing.

Figure 3:
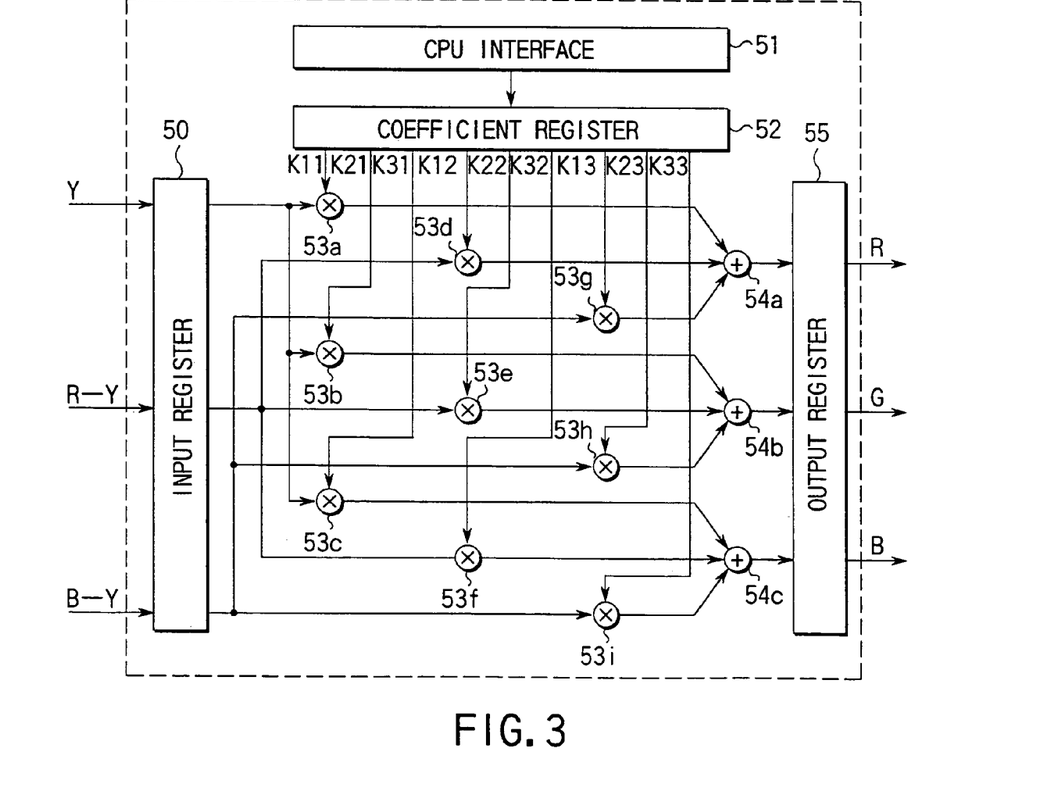
FIG. 3 is a block diagram showing the detailed arrangement of a color separation circuit 21 in FIG. 2.

FIG. 3 shows the detailed arrangement of the color separation circuit 21.

The color separation circuit 21 includes a CPU interface 51 for receiving an input from the CPU 31, a coefficient register 52 for holding the color matrix coefficients sent from the CPU 31, an input register 50 for holding signals from the Y/C separation circuit 18 and the like, and an output register 55 for holding the operation result obtained by performing a predetermined arithmetic operation based on the coefficients held by the coefficient register 52 using multipliers 53*a* to 53*i* and adders 54*a* to 54*c*.

According to this arrangement, a matrix operation is:

$$\begin{pmatrix} R \\ G \\ B \end{pmatrix} = \begin{pmatrix} k11 & k12 & k13 \\ k21 & k22 & k23 \\ k31 & k32 & k33 \end{pmatrix} \begin{pmatrix} Y \\ R-Y \\ B-Y \end{pmatrix}$$

This arithmetic operation attains processing that realizes color reproduction independent of the light source to be used, together with general white balance processing.

In the first embodiment, the user can select suitable one of the above color matrixes in accordance with the observation region and the type of light source to be used by operating the switch 34. This makes it possible to realize color reproduction desired by the user.

The second embodiment of the present invention will be described next.

Figure 4:
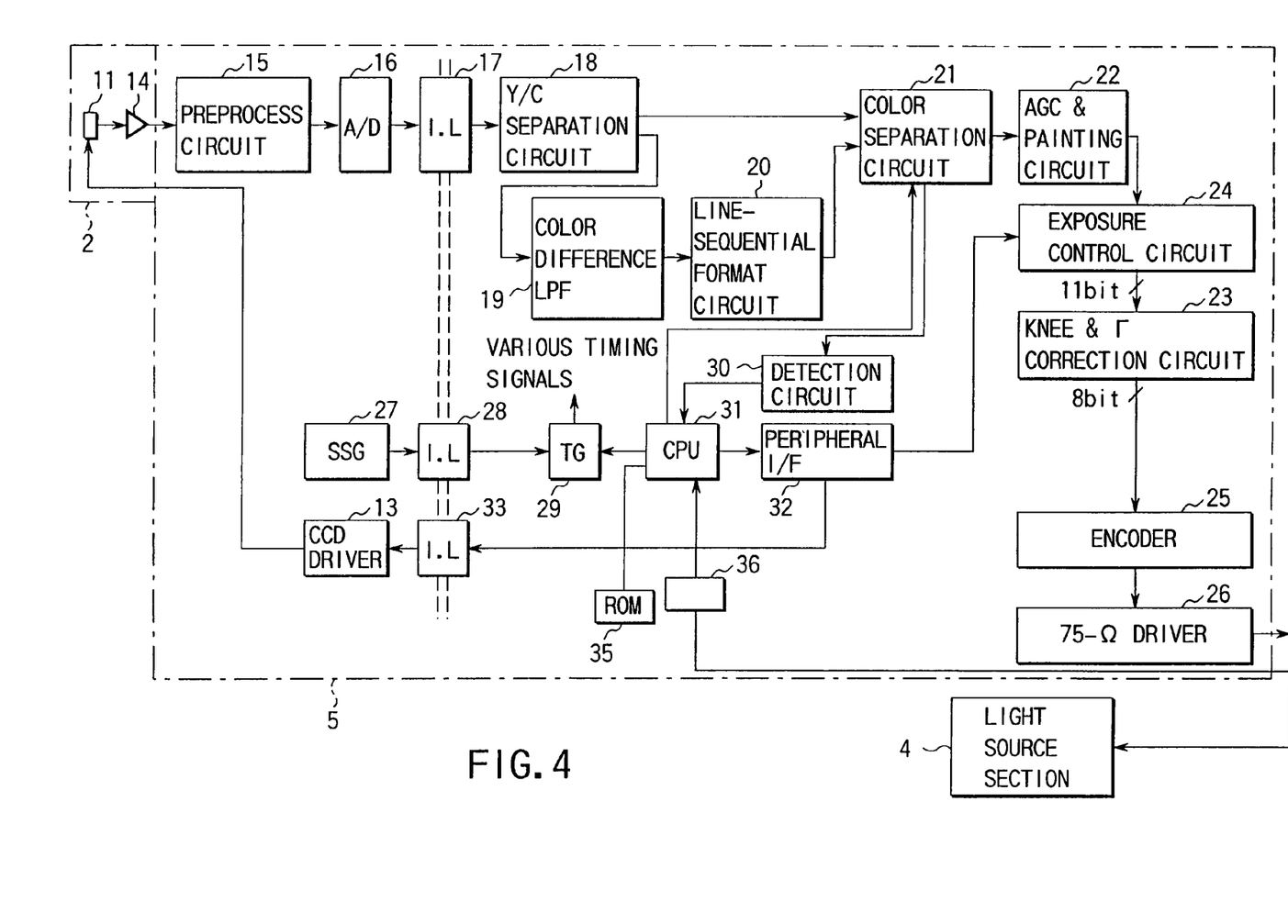
FIG. 4 is a block diagram showing the arrangement of an endoscope image sensing apparatus according to the second embodiment.

FIG. 4 shows the arrangement of the endoscope image sensing apparatus according to the second embodiment of the present invention. As shown in FIG. 4, this endoscope image sensing apparatus is characterized in that a light source section 4 and CPU 31 are connected to each other through a communication section 36 to communicate with each other. In this embodiment, the type of light source can be discriminated by serial communication.

The second embodiment is characterized in that the CPU 31 receives an identification signal from a light source by serial communication through the communication section 36, detects the type of light source on the basis of the identification signal, reads out a color matrix corresponding to the type of light source from a ROM 35, and outputs the matrix to a color separation circuit 21 to perform a predetermined arithmetic operation.

The remaining arrangements and functions are the same as those of the first embodiment, and hence a repetitive description will be avoided.

With the above processing, in the second embodiment, since a color matrix corresponding to the type of light source is automatically selected, and a predetermined arithmetic operation is performed, suitable color reproduction can be realized without distinction of the type of light source used, e.g., a halogen lamp, xenon lamp, or metal halide lamp.

The third embodiment of the present invention will be described next.

Since the arrangement of the endoscope image sensing apparatus according to the third embodiment is substantially the same as that of the first embodiment, a repetitive description will be avoided, and the characteristic feature of the third embodiment will be described below with reference to the arrangement in FIG. 2.

The third embodiment is characterized in that the type of light source is discriminated on the basis of the magnitude of a gain coefficient for white balance, and color matrixes are switched accordingly.

In general, since a metal halide light source emits bluish light, the gain value of a red light component becomes large upon white balance adjustment. A halogen light source emits yellowish light. In this case, therefore, the gain value of a blue light component becomes large upon white balance adjustment.

In the third embodiment, in consideration of the characteristics of each light source described above, the light source used is discriminated in accordance with the gain value, and color matrixes are switched accordingly.

Figure 5:
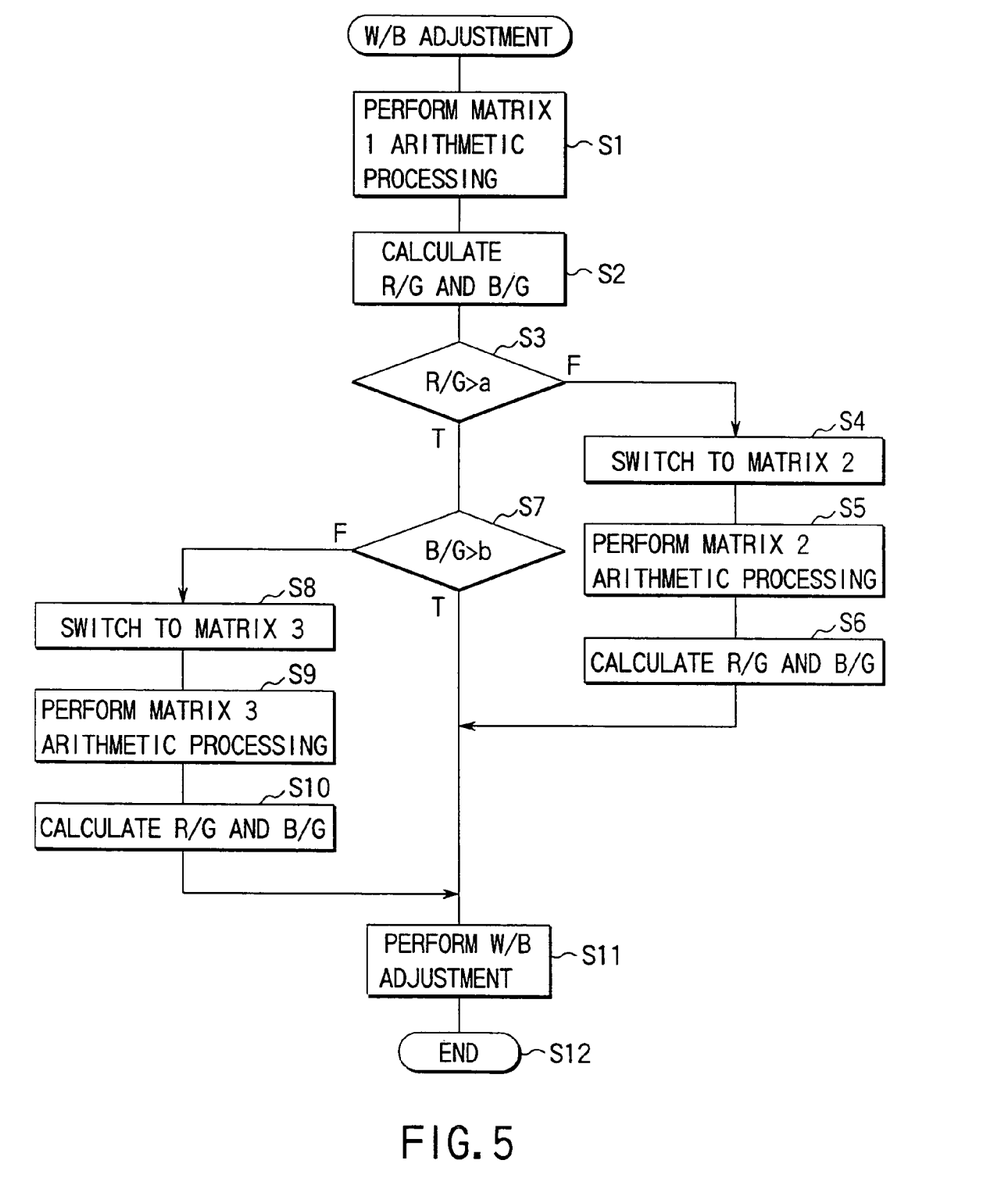
FIG. 5 is a flow chart showing a matrix switching sequence in an endoscope image sensing apparatus according to the third embodiment.

A color matrix switching sequence will be described in detail below with reference to the flow chart of FIG. 5. First of all, arithmetic processing is performed by using color matrix 1. In this case, a CPU 31 reads out color matrix 1 that is held in a ROM 35 assuming the use of a xenon lamp, which is used most widely, and performs predetermined arithmetic processing in a color separation circuit 21 on the basis of color matrix 1 (step S1).

The CPU 31 then calculates gain values G/R and B/G (step S2). If the gain value R/G is smaller than a predetermined value a, since it indicates the gain value of a red light component is large, the CPU 31 determines that a metal halide lamp is used, and reads out color matrix 2 corresponding to the metal halide lamp from the ROM 35 (step S4). The CPU 31 then performs predetermined arithmetic processing in the color separation circuit 21 on the basis of color matrix 2 (step S5). The CPU 31 computes the gain values R/G and B/G again (step S6).

If the gain value B/G is smaller than a predetermined value b (step S7), since it indicates that the gain value of a blue light component is large, the CPU 31 determines that a halogen lamp is used, and reads out color matrix 3 corresponding to a halogen lamp from the ROM 35 (step S8). The CPU 31 then performs predetermined arithmetic processing in the color separation circuit 21 on the basis of color matrix 3 (step S9). The CPU 31 computes the gain values R/G and B/G again (step S10). In this manner, the CPU 31 performs a predetermined white balance adjustment on the basis of the above gain value (step S11), and then terminates the operation.

A color matrix computation and white balance adjustment for color reproduction are simultaneously implemented by one color separation circuit 21 like the one shown in FIG. 3. If a matrix computation corresponding to a general-purpose light source is performed, the gain coefficient obtained when white balance processing is performed is fed back to the CPU 31. The CPU 31 then recognizes the light source used in accordance with the gain coefficient. Upon determining that the color matrix is not suitable, the CPU 31 reads out a suitable color matrix from the ROM 35, and the color separation circuit 21 executes a matrix computation again. With the above sequence as an example, color reproduction is realized independently of the type of light source used.

A modification of the first embodiment will be described finally.

Figure 6:
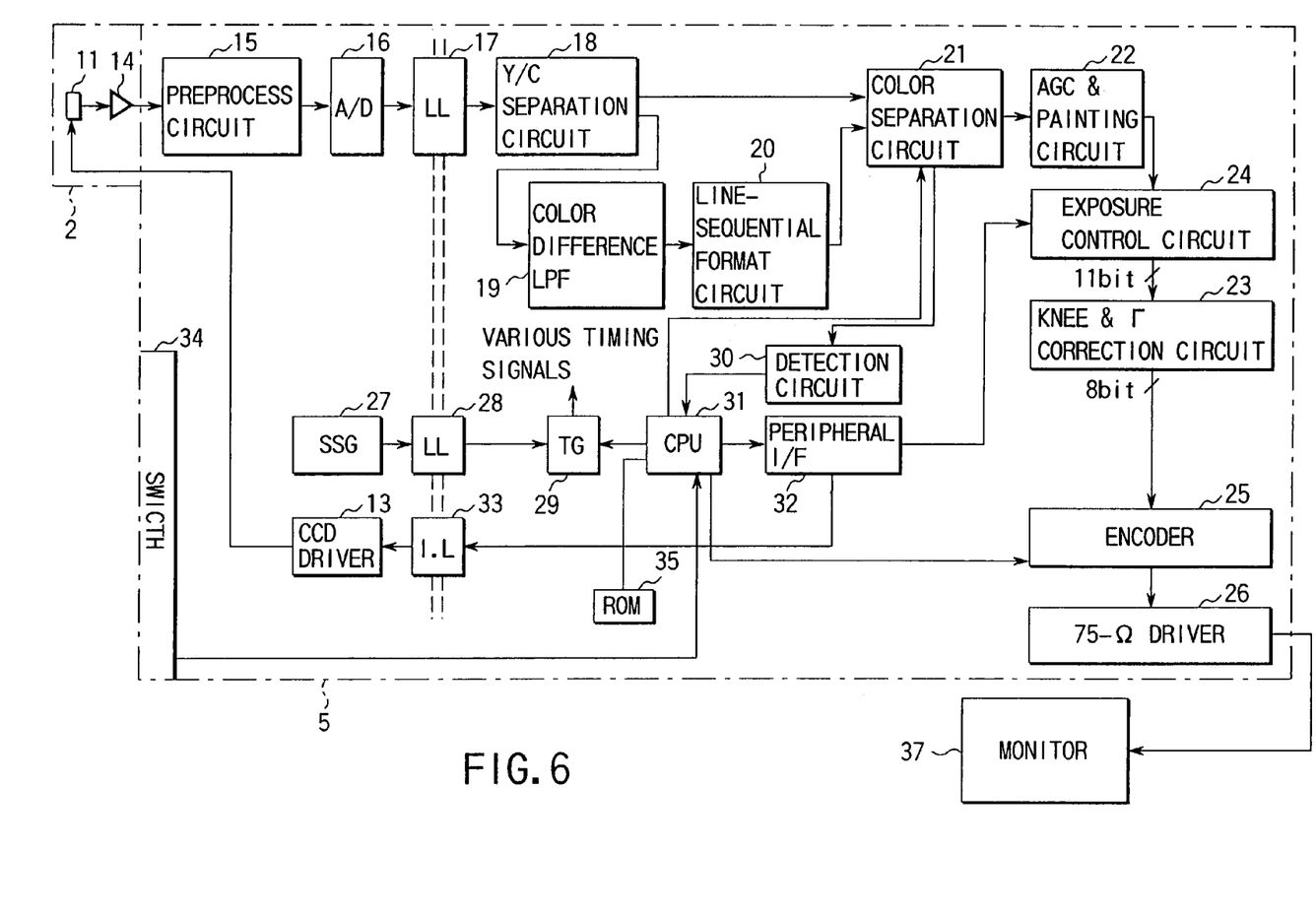
FIG. 6 is a block diagram showing the arrangement of a modification of the first embodiment.
Figure 7:
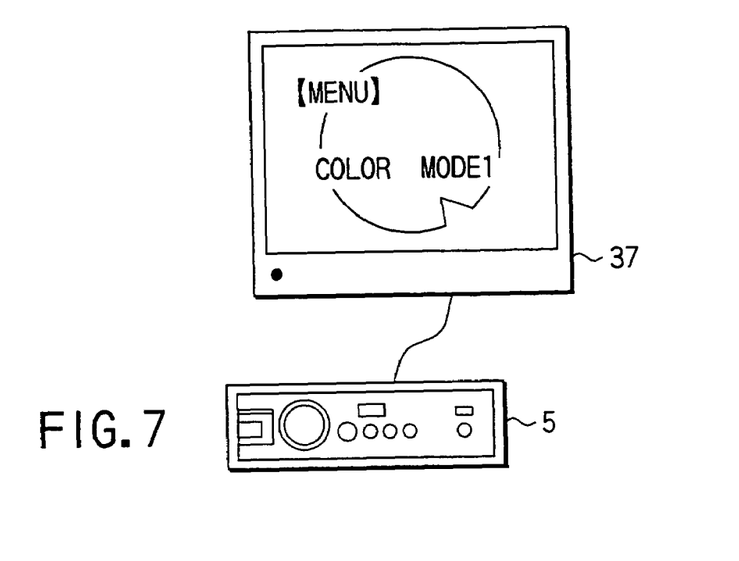
FIG. 7 is a view showing an example of how a menu is displayed on a monitor 37 in FIG. 6.

FIG. 6 is a block diagram showing the arrangement of an endoscope image sensing apparatus according to a modification of the first embodiment. FIG. 7 shows an example of a display menu.

This modification is characterized in that a monitor 37 for displaying an observation image is connected to the apparatus to display the contents to be selected with the switch 34 are displayed superimposed on the observation image on the monitor 37.

FIG. 7 shows an example of the display, in which display menu [MENU] COLOR MODE 1 is displayed superimposed on the observation image.

According to this modification, since the contents to be selected can be displayed on the screen of the monitor 37, a setting error and the like caused by the user can be prevented.

The embodiments of the present invention have been described above. However, the present invention is not limited to them, and various changes and modifications can be made without departing from the spirit and scope of the invention. For example, in each embodiment described above, a one-chip color CCD is used. Obviously, however, a three-chip color CCD can be used. In addition, the metal halide lamp serving as the light source includes an AC metal halide lamp and DC metal halide lamp.

The effects of the first to third embodiments will be summarized below.

According to the first embodiment of the present invention, one of the color matrixes stored in the ROM 35 as a storage means is selected on the basis of the operation of the switch 34 as a designating means operated by the user, and the CPU 31 as a control means outputs the selected matrix to the color separation circuit 21 as a conversion matrix means. As a consequence, the color separation circuit 21 converts the luminance and color difference signals into primary color signals.

According to the modification of the first embodiment, since the contents to be selected can be displayed on the screen of the monitor 37 as a display means, a setting error and the like caused by the user can be prevented.

According to the second embodiment, the CPU 31 as a control means performs serial communication with the light source section 4 through the communication section 36 as a communication means, and recognizes the type of light source on the basis of the identification signal sent from the light source section 4. Coefficients associated with a color matrix corresponding to the recognized type are readout from the ROM 35 as a storage means and output to the color separation circuit 21 as a conversion matrix means. The luminance and color difference signals are then converted into primary color signals on the basis of the color matrix.

According to the third embodiment, the CPU 31 as a control means discriminates the type of light source in accordance with the magnitude of the coefficient used for a white balance adjustment, and reads out coefficients associated with the color matrix corresponding to the type from the ROM 35. The coefficients are output to the color separation circuit 21 as a conversion matrix means, and the luminance and color difference signals are converted into primary color signals on the basis of the color matrix.

As described above, according to the present invention, first, optimal color reproduction can be realized in accordance with the regions of interest such as a region with heavy bleeding, a region with a lot of fat, or a substantially white region, e.g., a joint, the technique used, the preference of the user, or the like. Second, differences in color reproduction due to different types of light sources, e.g., a halogen lamp, xenon lamp, or metal halide lamp, are absorbed to realize consistent color reproduction independent of the types of light sources.

According to the present invention, therefore, there is provided an endoscope image sensing apparatus which can switch suitable color matrixes depending on the type of an observation region, the type of light source used, or the like, and can obtain excellent color reproduction corresponding to the type of observation region or the type of light source used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope image sensing apparatus comprising:
   an image sensing device for imaging an object to obtain an image signal, and outputting the image signal;
   a storage section for storing a plurality of color matrices each corresponding to a plurality of color tones for displaying an observation image of the object on a display section;
   a color adjustment processing section for performing color adjustment processing;
   a recognition section for recognizing a kind of light source to be used in irradiation of the object based on data at the time of the color adjustment processing;
   a selecting section for selecting a color matrix from the plurality of color matrices for displaying the observation image in a color tone according to a recognition result of the recognition section; and
   a computing section for performing computation using the selected color matrix to convert the image signal output from the image sensing device to a color component signal.

2. The apparatus according to claim 1, wherein the image sensing device comprises a color CCD.

3. The apparatus according to claim 1, wherein said kind of light source includes at least one of a xenon lamp, halogen lamp, and a metal halide lamp.

4. The apparatus according to claim 1, wherein the color adjustment processing comprises white balance processing.

5. An endoscope image sensing apparatus comprising:
   an image sensing device for imaging an object to obtain an image signal, and outputting the image signal;

a storage section for storing a plurality of color matrices each corresponding to a plurality of color tones for displaying an observation image of the object on a display section;

a recognition section for receiving an identification signal corresponding to a kind of light source to be used in irradiation of the object, and recognizing the kind of light source based on the identification signal;

a selecting section for selecting a color matrix from the plurality of color matrices for displaying the observation image in a color tone according to a recognition result of the recognition section; and a computing section for performing computation using the selected color matrix to convert the image signal output from the image sensing device to a color component signal.

6. An endoscope image sensing apparatus comprising:

an image sensing device for imaging an object to obtain an image signal, and outputting the image signal; and a processor for performing processing of the image signal, the processor comprising:

a storage section for storing a plurality of color matrices each corresponding to a plurality of color tones for displaying an observation image of the object on a display section;

a color adjustment processing section for performing color adjustment processing;

a recognition section for recognizing a kind of light source to be used in irradiation of the object based on data at the time of the color adjustment processing;

a selecting section for selecting a color matrix from the plurality of the color matrices for displaying the observation image in a color tone according to a recognition result of the recognition section; and a computing section for performing computation using the selected color matrix to convert the image signal output from the image sensing device to a color component signal.

7. An endoscope image sensing method comprising:

imaging an object to obtain an image signal, and outputting the image signal;

recognizing a kind of light source to be used in irradiation of the object;

selecting a color matrix from a plurality of color matrices for displaying the observation image in a color tone according to a result of the recognition; and performing computing using the selected color matrix to convert the output image signal to a color component signal;

wherein the kind of light source is recognized based on data at the time of computation.

8. An image sensing method comprising:

imaging an object to obtain an image signal, and outputting the image signal;

receiving an identification signal corresponding to a kind of light source to be used in irradiation of the object, and recognizing the kind of light source based on the identification signal;

selecting a color matrix from a plurality of color matrices for displaying the observation image in a color tone according to a result of the recognition; and performing computing using the selected color matrix to convert the output image signal to a color component signal.

9. An endoscope image sensing apparatus comprising:

an image sensing device for imaging an object to obtain an image signal, and outputting the image signal; and a processor for performing processing of the image signal, the processor comprising:

a storage section for storing a plurality of color matrices each corresponding to a plurality of color tones for displaying an observation image of the object on a display section;

a recognition section for receiving an identification signal corresponding to a kind of light source to be used in irradiation of the object, and recognizing the kind of light source based on the identification signal;

a selecting section for selecting a color matrix from the plurality of color matrices for displaying the observation image in a color tone according to a recognition result of the recognition section; and a computing section for performing computation using the selected color matrix to convert the image signal output from the image sensing device to a color component signal.

* * * * *